United States Patent [19]

Singer et al.

[11] Patent Number: 5,219,323
[45] Date of Patent: Jun. 15, 1993

[54] METHOD AND APPARATUS FOR ROTATING A WRIST

[75] Inventors: Robert D. Singer, Clive; Ernest A. Trickey, Des Moines, both of Iowa

[73] Assignee: ElectroBionics Corporation, Ankeny, Iowa

[21] Appl. No.: 718,774

[22] Filed: Jun. 21, 1991

[51] Int. Cl.⁵ .................................................. A61F 5/10
[52] U.S. Cl. ........................................ 602/16; 602/20; 602/21; 128/25 R; 623/61
[58] Field of Search ............. 602/5, 16, 20, 21, 23-27, 602/29; 128/25 R, 26, 881; 623/57, 59, 61; 482/94, 139

[56] References Cited

U.S. PATENT DOCUMENTS

| 43,590 | 7/1864 | Koeller | 623/61 X |
|---|---|---|---|
| 2,135,018 | 11/1938 | Svensson | 482/94 |
| 2,542,316 | 2/1951 | Farrar, Jr. | 623/61 |
| 2,626,398 | 1/1953 | Grindle et al. | 623/59 |
| 2,767,708 | 10/1956 | Keropian | 602/21 |
| 3,089,700 | 5/1963 | Hotas | 482/94 |
| 3,683,897 | 8/1972 | Shield et al. | 128/25 R |
| 3,707,963 | 1/1973 | Keropian | 602/21 |
| 4,237,873 | 12/1980 | Terry et al. | 602/20 |
| 4,433,679 | 2/1984 | Mauldin et al. | 602/20 X |
| 4,538,595 | 9/1985 | Hajianpour | 128/25 R |
| 4,559,932 | 12/1985 | Salort | 602/20 |
| 4,612,919 | 9/1986 | Best | 602/16 |
| 4,651,719 | 3/1987 | Funk et al. | 602/20 X |
| 4,669,451 | 6/1987 | Blauth et al. | 128/25 R |
| 4,809,688 | 3/1989 | Aymerica del Valle et al. | 602/21 |
| 5,002,044 | 3/1991 | Catter | 602/21 X |
| 5,117,814 | 6/1992 | Luttrell et al. | 128/25 R |

Primary Examiner—Richard J. Apley
Assistant Examiner—Linda C. M. Dvorak
Attorney, Agent, or Firm—Schwartz & Weinrieb

[57] ABSTRACT

Apparatus and methods of rotating a non-functioning wrist by flexing or extending the associated elbow may be activated by muscle action of the wearer or by an elbow actuator. Cuffs above and below the elbow that receive the wrist and arm are interlinked in a manner that permits varying of the degree of supination and pronation of the wrist to the needs of the wearer. Also, the angle of elbow flexion at which wrist rotation starts and stops can be varied by adjusting the operating mechanism.

20 Claims, 8 Drawing Sheets

METHOD AND APPARATUS FOR ROTATING A WRIST

BACKGROUND OF THE INVENTION

This invention relates to orthotic and rehabilitative rotation of the human wrist, and more particularly to methods and apparatus that rotate a wrist to varying degrees depending on the amount of flexion of the associated elbow.

Equipment used for rotating human wrists in the past has been complicated and cumbersome. Some of these devices have substituted spring mechanisms for human muscles. These systems provide either inward (pronation) or outward (supination) rotation, but not both. Also, clothing can not be worn over orthotic equipment when it is large and bulky or when the clothing could become entangled in moving parts.

OBJECTIVES OF THE INVENTION

Accordingly, it is an object of this invention to provide improved methods and apparatus for rotating a human wrist.

Another object is to provide easily adjustable and customizable methods and apparatus for turning a wrist.

A further object is to provide wrist rotation methods and apparatus that permit functional use of a paralyzed wrist and can provide controlled therapeutic pronation/supination continuous passive motion for rehabilitating an arm or wrist following surgery or trauma.

Another object is to provide wrist rotation apparatus that encapsulates a significant area of the arm yet is small enough to fit under a loose fitting shirt.

An additional object is to provide methods and apparatus that smoothly articulate a wrist to a predetermined degree of inward or outward rotation as a person flexes or extends the elbow.

Another object is to provide wrist rotation methods and apparatus that may be powered either by a person flexing or extending an elbow, or by an electronic actuator controlled by such a person.

A further object is to provide wrist rotation apparatus and methods that enable a person lacking a functional wrist to perform activities of daily living, such as combing hair, feeding themself, and shavging both sides of the face.

An additional object is to provide relatively simple and low cost, durable, easily maintained wrist rotating apparatus and methods that are portable and can be easily attached and removed, and which do not possess defects found in similar prior art devices and methods.

Other objects and advantages of the invention will be found in the specification and claims, and the scope of the invention will be set forth in the claims.

DESCRIPTION OF THE INVENTION

The drawing shows pronation/supination apparatus 1 for orthotics and continuous passive motion that rotates a non-functioning human wrist 2 medially and laterally about the longitudinal axis of the arm when an elbow 3 is flexed or straightened. A humeral cuff 5 receives the upper arm 6 above the elbow, a distal forearm cuff 7 receives the wrist 3 and may extend to the palmar arch, and a proximal forearm cuff 8 receives the forearm 9 between cuffs 5 and 7 below elbow 3.

Humeral cuff 5 and proximal forearm cuff 8 are hinged to each other at 10 and 11 to permit movement when elbow 3 is flexed and extended, preferably at least ninety degrees of movement. A bolt 12 passing through cuffs 5 and 8 and bushing nut 13 provide hinge means at 10, and a bolt 14 and bushing nut 15 provide the hinge means at 11. The edges of cuffs 5 and 8 are curved away from each other between hinge means 10 and 11 to define an opening 16 for the wearer's elbow.

Proximal forearm cuff 8 and distal forearm cuff 7 are connected by an elongated flexible medial stay 18 and an identical lateral stay 19 that permit rotation of cuff 7 with respect to cuff 8, and preferably about ninety degrees of rotation. One end of each stay is pivotally connected to cuff 8 by a nut 20 and a bolt bushing 21, and the opposite end of each stay is pivotally connected to cuff 7 by a nut 22 and a bushing bolt 23. A pair of identical bushings 25 at about the center of stays 18 and 19 guide the rotational movement of distal forearm cuff 7. Each bushing may employ a nut 26 and a bolt 27 that hold a pair of flexible plastic guide washers 28 on opposite surfaces of the adjacent cuffs. The terminal edges of cuffs 7 and 8 are scalloped to define curved radial guide surfaces 29 and 30 that facilitate rotation of cuff 7.

Humeral cuff 5, proximal forearm cuff 8 and distal forearm cuff 7 are connected to each other by leverage means 33 that causes distal forearm cuff 7 to rotate wrist 2 when elbow 3 is flexed and extended. Means 33 includes bell crank 34, lever 35 and linkage means 36 connecting the bell crank to the lever. One end 37 of bell crank 34 is pivotally attached to distal forearm cuff 7 by a nut 38 and a bushing bolt 39 that passes through cuff 7. The pivot axis 40 of the bell crank is located on proximal forearm cuff 8 at another end 41, and the axis is provided by nut 42 and a bushing bolt 43 that passes through the bell crank and cuff 8. A flexible washer 44 may be located between bell crank 34 and cuff 8. A guide bushing 45 that is identical to bushings 25 is located between cuffs 7 and 8 at about the center of bell crank 34. A bolt 46 passing through cuff 5 and nut 47 secure one end 48 of lever 35 to cuff 5. Bushing bolt 14 of hinge means 11 passes through lever 35, and the opposite end 50 of the lever extends over proximal forearm cuff 8 beyond where the ends of cuffs 5 and 8 are hinged to each other. Linkage means 36 may include a metal rod or link 51 that is bent to conform to the shape of cuff 8. One end 52 of rod 51 is passed up through the underside of lever end 50 and may be pivotally connected to lever 35 by a cap nut 53. Rod end 52 does not move when elbow 3 is flexed or extended. The opposite end 54 of rod 51 passes up through the underside of bell crank 34 adjacent pivot axis 40, and may be pivotally connected to the bell crank by a cap nut 55. Rod end 54 is located between wrist 2 and elbow 3 a predetermined distance D from pivot axis 40.

When elbow 3 is flexed, rod 51 pulls on bell crank 34 and pivots its end 41 around axis 40 toward the wearer's elbow 3. This pulls crank end 37 toward the open side of distal forearm cuff 7 and supinates or rotates cuff 7 outwardly in a smooth steady motion. When elbow 3 is extended, rod 51 pushes on bell crank 34 and pivots its end 41 around axis 40 away from the wearer's elbow 3. This pushes crank end 37 away from the open side of distal forearm cuff 7 and pronates or rotates cuff 7 inwardly in a smooth steady motion.

Figure 1:
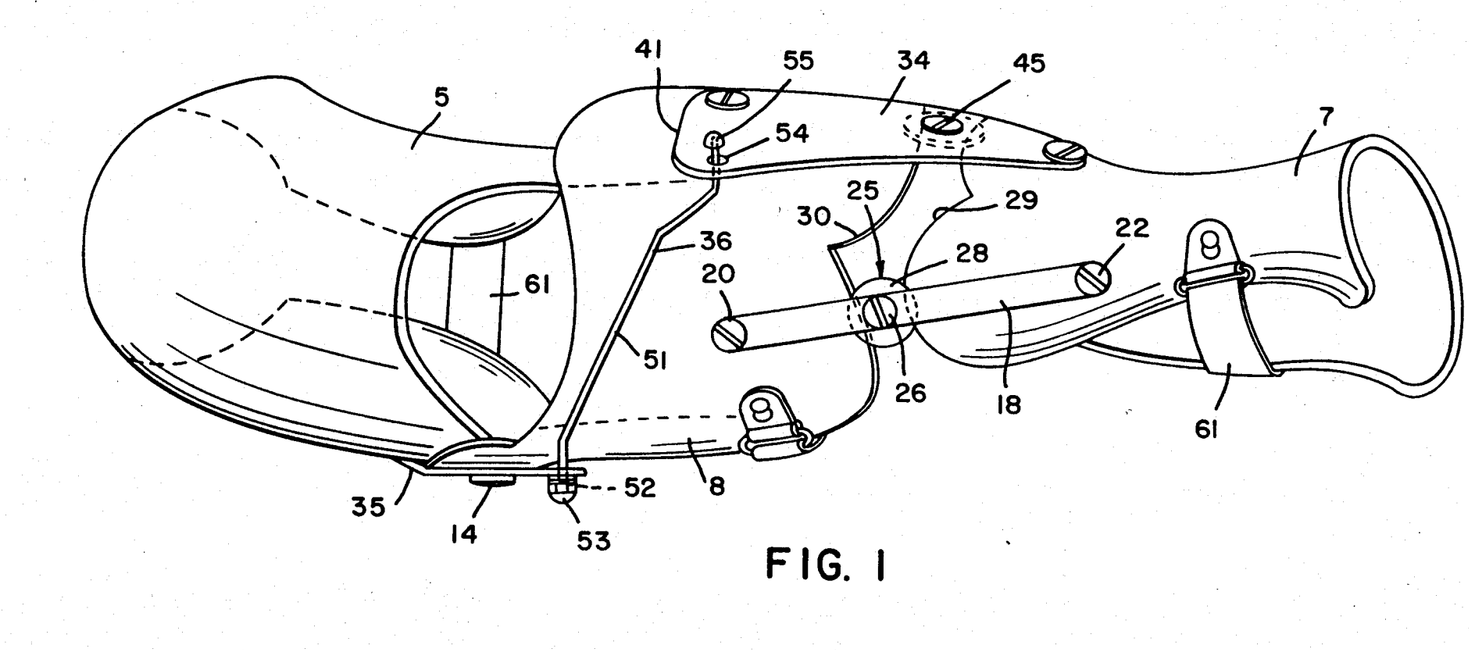
FIG. 1 is a perspective view of the apparatus in accord with this invention.
Figure 2:
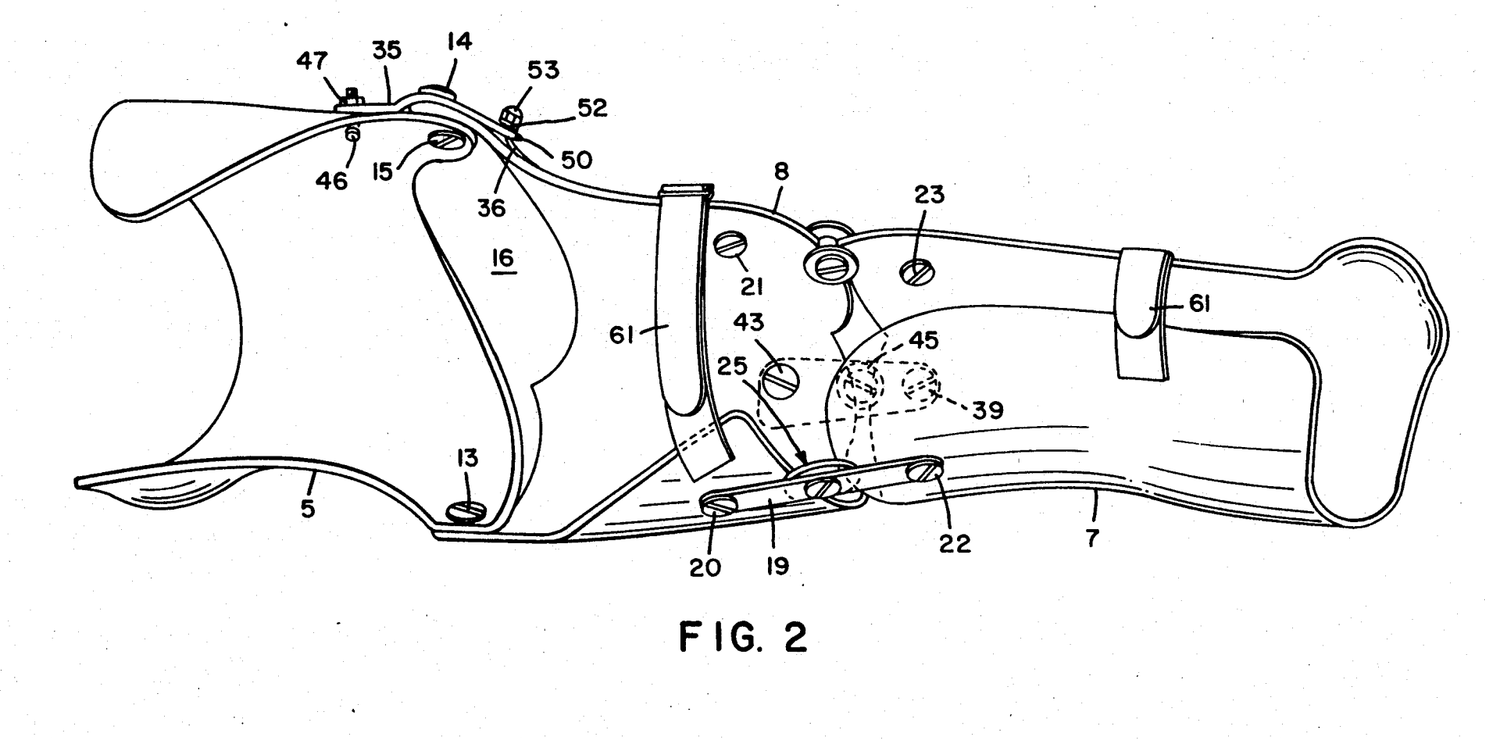
FIG. 2 is a top view of the apparatus shown in FIG. 1.
Figure 3:
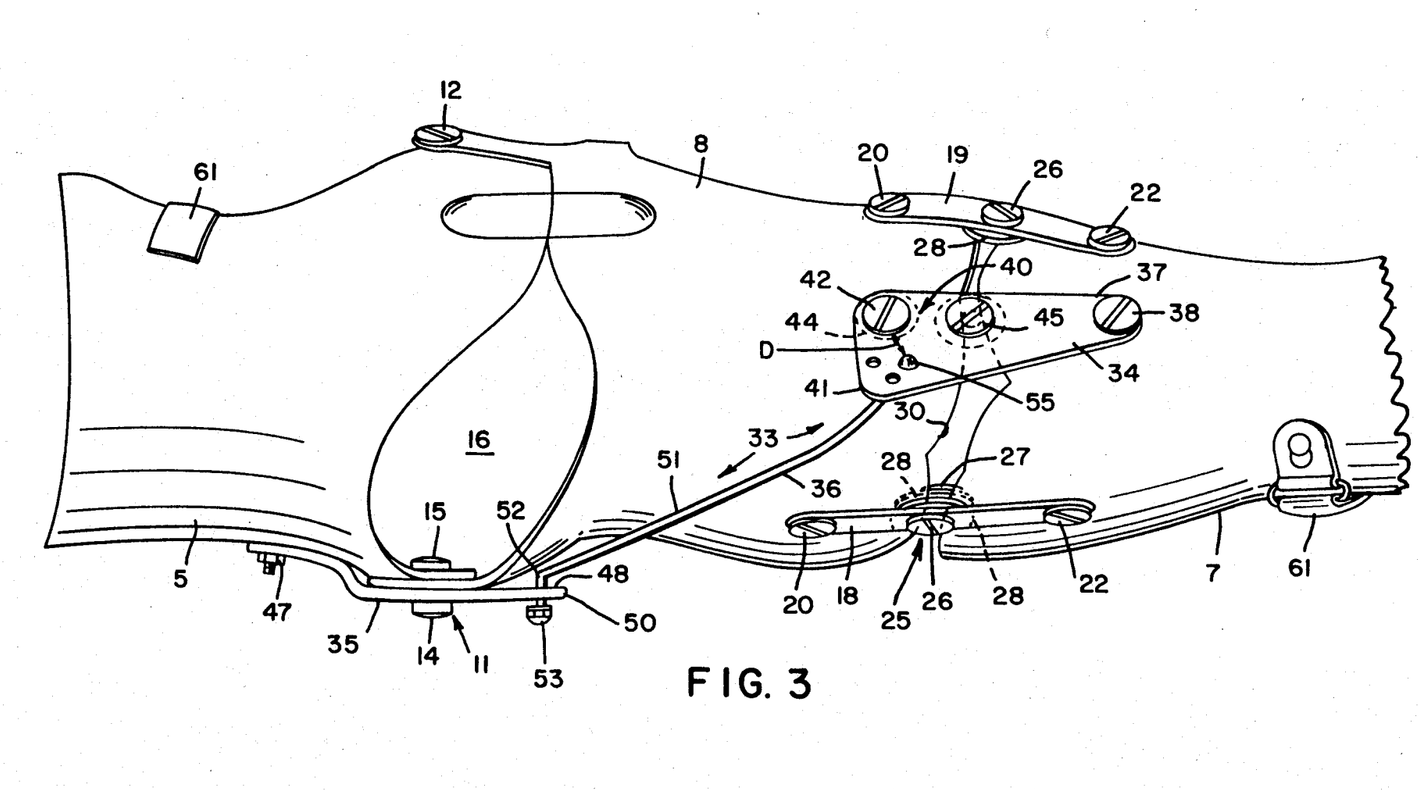
FIG. 3 is a bottom view of the apparatus shown in FIG. 1.
Figure 4:
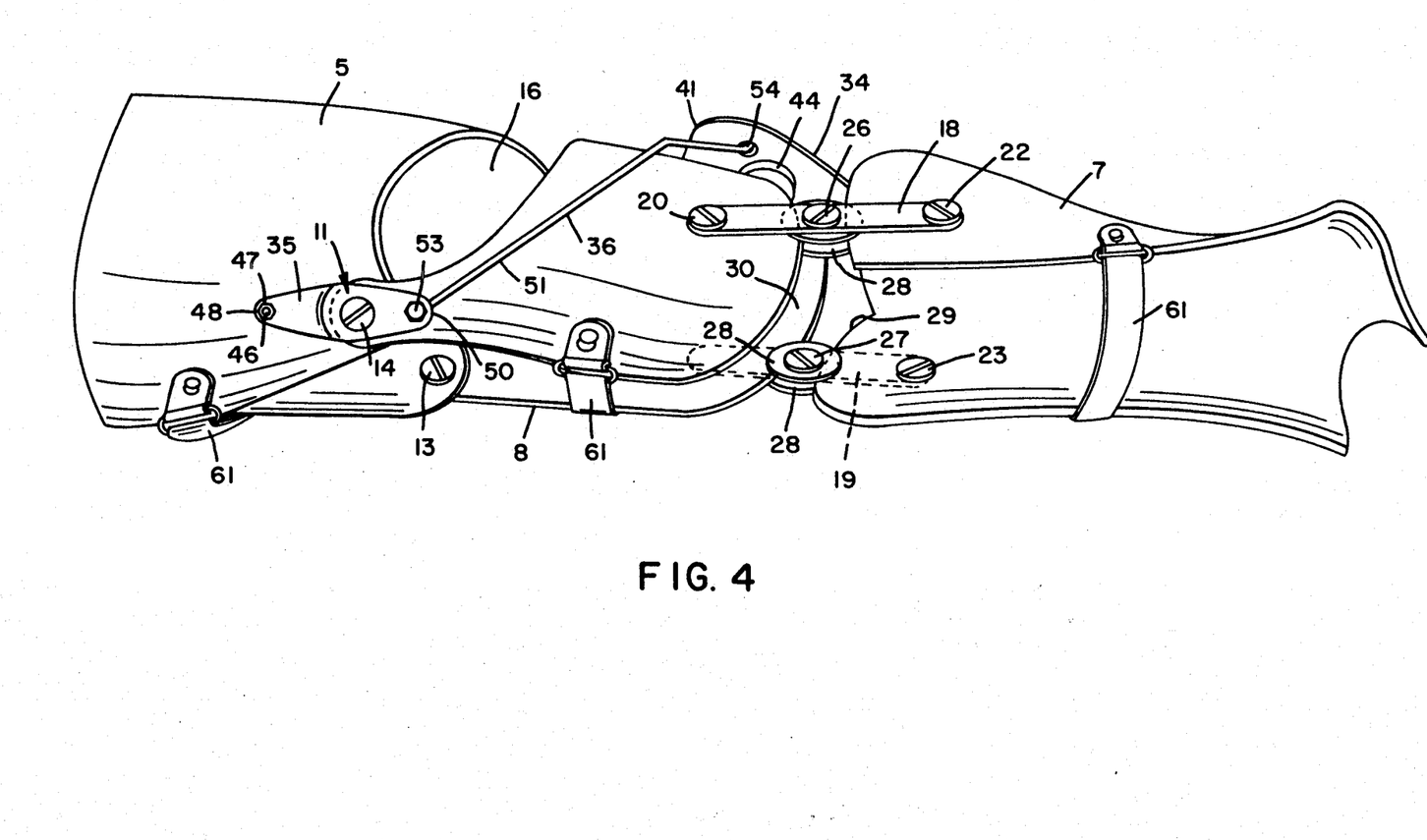
FIG. 4 is a view of one side of the apparatus in FIG. 1.
Figure 5:
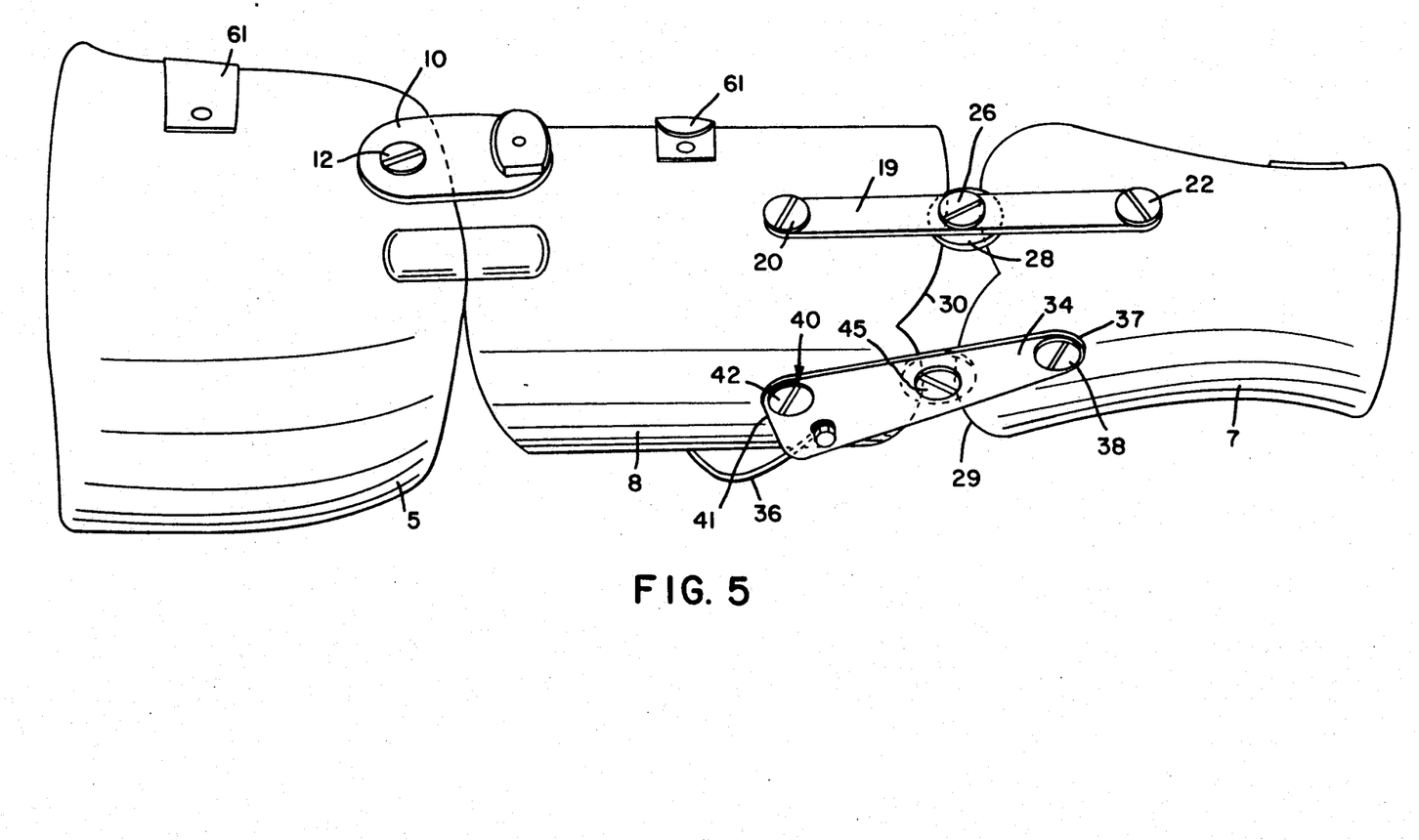
FIG. 5 is a view of the opposite side of the apparatus in FIG. 1.
Figure 6:
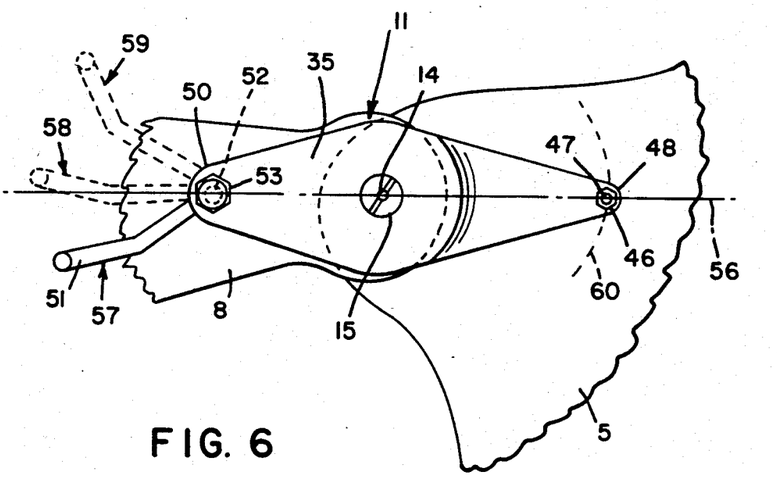
FIG. 6 is an enlarged broken away view of the lever and linkage from the embodiment of FIG. 1.

This invention permits the degree of wrist rotation and the point at which a wrist rotation begins and stops rotating to be adjusted or customized for a specific person. The degree of rotation of distal forearm cuff 7 may be varied by varying the distance D separating the point of attachment of rod end 54 and pivot axis 40. Increasing distance D will decrease the degree of rotation of cuff 7 and decreasing distance D will increase its rotation. The amount of elbow flexion that occurs before rotation begins can be varied by varying the point on humeral cuff 5 at which lever end 48 is attached. As shown in FIG. 6, bolt 46 and bushing bolt 14 and rod end 52 all lie on a common line 56 at about the center of lever 35. As rod 51 moves across line 56, the action of bell crank 34 either begins or stops. When an elbow 3 is moved from an extended position toward a flexed position, rod 51 would move from its elbow extended position 57 toward an elbow flexed position 58 where its end is approximately aligned with line 56. As rod 51 crosses line 56 moving toward another elbow flexed position 59, rotation of distal forearm cuff 7 and wrist 2 begins. As rod 51 is moved from an elbow flexed position 59 to its position 58 aligned with line 56, rotation of distal forearm cuff 7 and wrist 2 stops. The degree of elbow flexion at which wrist rotation begins and stops can be varied by changing the point at which lever end 48 is attached to humeral cuff 5. This will change the angle of line 56 with respect to rod 51 and the other components. The possible points of attachement lie on an arc 60 that has bolt 14 in hinge 11 at its center, and bolt 14 defines a turning point for pivoting end 48 and relocating bolt 47 on arc 60. Turning lever 35 so as to move bolt 47 in a clockwise direction on arc 60 will require more elbow flexion before wrist rotation begins and stops, and moving bolt 47 in a counterclockwise direction will decrease the amount of elbow flexion required.

Cuffs 5, 7 and 8 may be made from a lightweight relatively rigid though flexible synthetic plastic material that can be formed or adjusted to conform to the shape of the body of the wearer. Each cuff is roughly U-shaped in cross section to permit insertion and removal of an arm and wrist. At least one hook and loop closure strap 61 should be attached to each of cuffs 5, 7 and 8 in conventional manner so that the straps span the open ends of the cuffs for holding apparatus 1 on its wearer.

Figure 7:
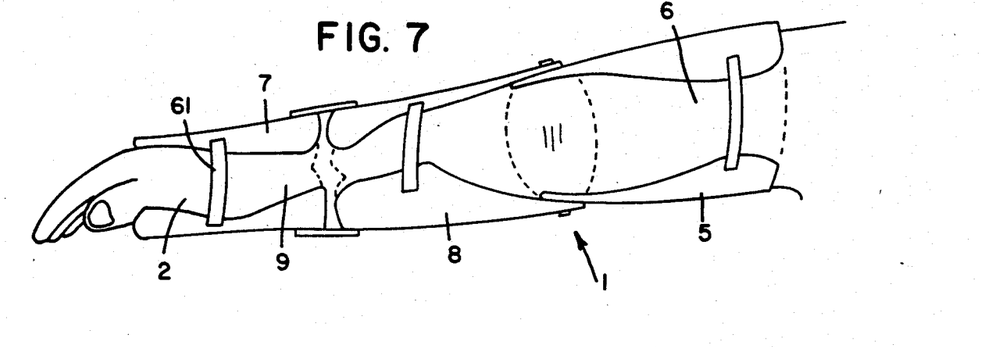
FIG. 7 is a view of the embodiment of FIG. 1 on an arm with the elbow fully extended.
Figure 8:
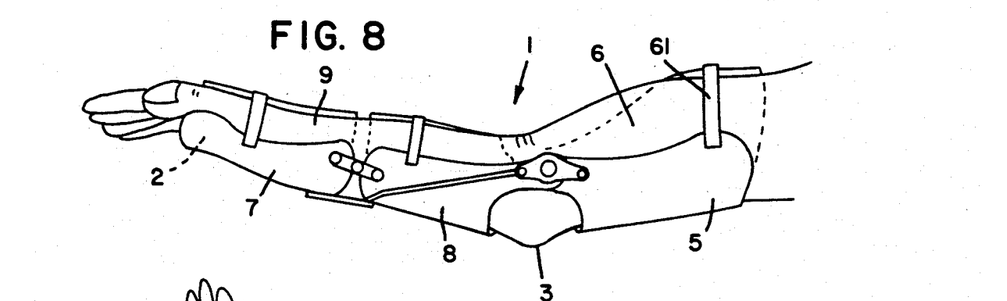
FIG. 8 is a view corresponding to FIG. 7 with the elbow partially flexed.
Figure 9:
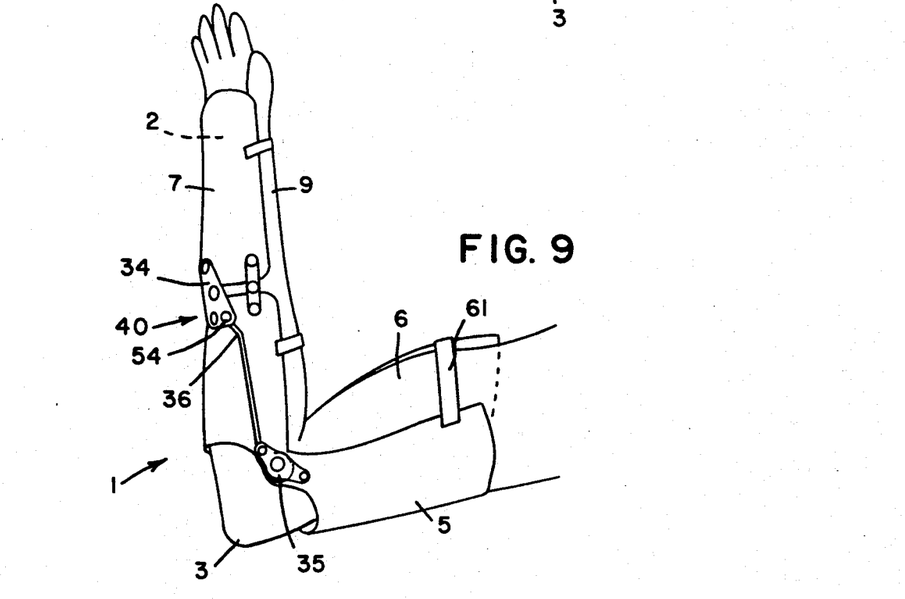
FIG. 9 is a view corresponding to FIGS. 7 and 8 with the elbow essentially fully flexed.
Figure 10:
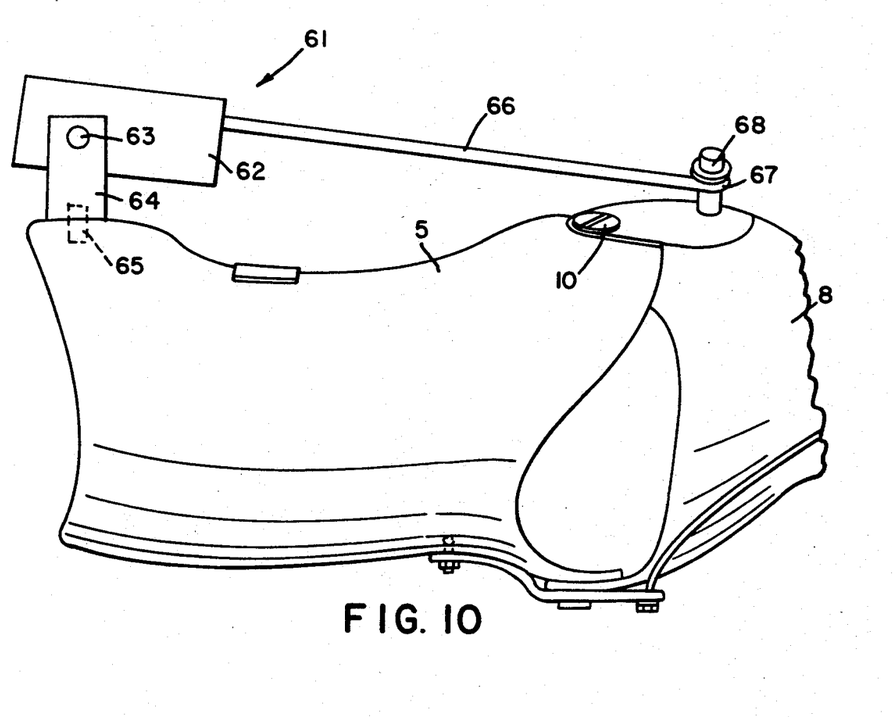
FIG. 10 is a partial bottom view corresponding to FIG. 3 of another embodiment of the invention.
Figure 11:
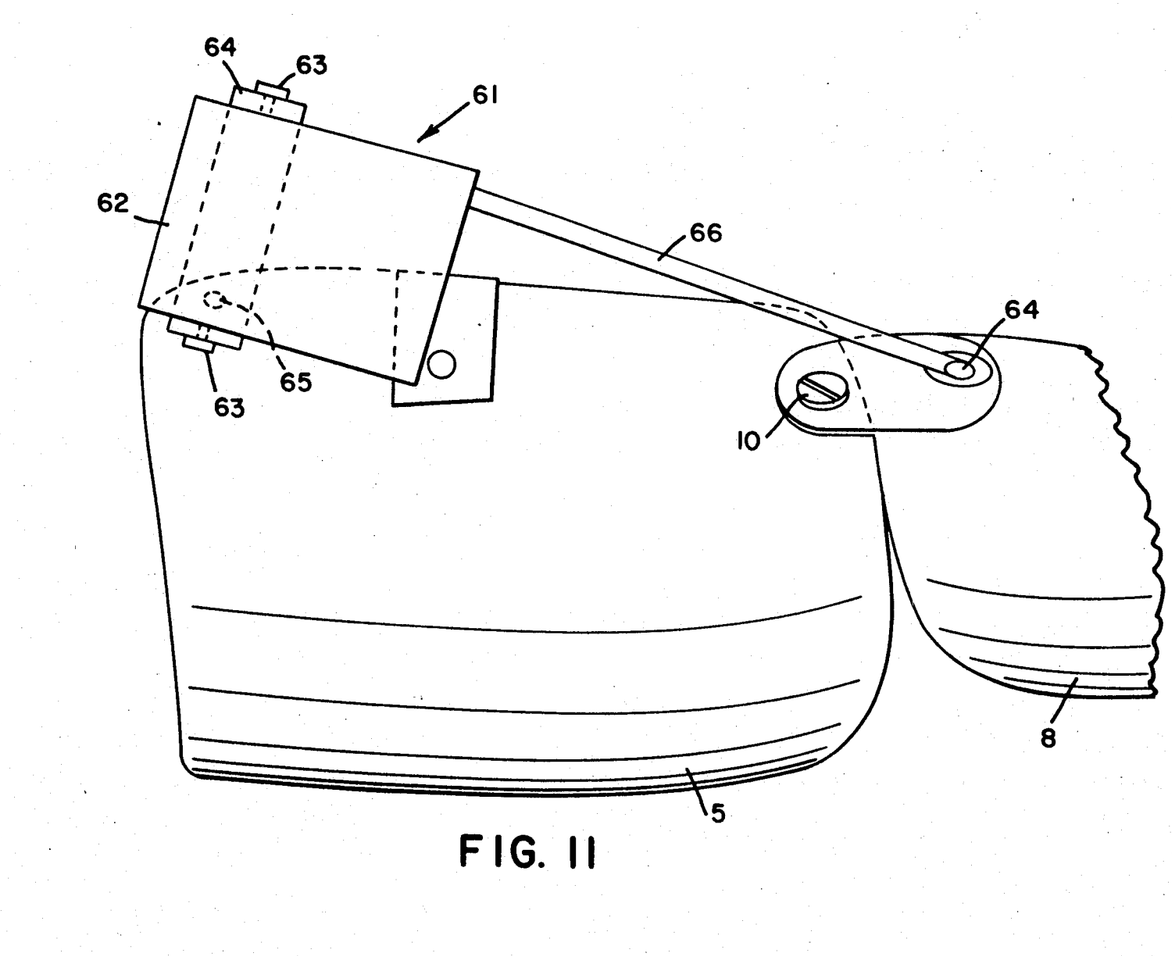
FIG. 11 is a partial side view corresponding to FIG. 5 of the embodiment of FIG. 10.

FIGS. 10 and 11 show another embodiment of the invention that may be used by a person who can not flex or extend an elbow. This embodiment is identical in all respects to the embodiment of FIGS. 1-9, except that motorized means 61 has been added for causing an elbow to flex and extend. Motorized means 61 may be an electronic range of motion apparatus as disclosed in U.S. application for Pat. Ser. No. 07/301,539, filed Jan. 24, 1989, and shown in FIGS. 7 and 8 thereof. The electronic range of motion apparatus has an actuator 62 that may be pivotally attached at one end by bolts 63 to a gimbal bracket 64. A bolt 65 holds bracket 64 on humeral cuff 5 and permits forward and backward rotation of the bracket. A ram 66 extends from actuator 62 and has its end 67 pivotally attached to a lug 68 that has been secured to proximal forearm cuff 8 adjacent to hinge 10. When actuator 62 pulls ram end 68 in toward the actuator, the cuffs 7 and 8 pivot toward cuff 5, and apparatus 1 functions as described when the wearer flexes elbow 3. When actuator 62 pushes ram end 68 away from the actuator, cuffs 7 and 8 pivot away from cuff 5, and apparatus 1 functions as described when the wearer extends elbow 3.

This invention also includes methods of rotating a wrist 2 of a human arm by attaching distal forearm cuff 7 to wrist 2, attaching humeral cuff 5 to the arm above elbow 3, and attaching proximal forearm cuff 8 to the arm below elbow 3 between distal forearm cuff 7 and humeral cuff 5. Hinging of humeral cuff 5 and proximal forearm cuff 8 to each other at 10 and 11 enables cuffs 5 and 8 to pivot when elbow 3 is flexed and extended. Distal forearm cuff 7 is connected to proximal forearm cuff 8 so that cuff 7 can rotate relative to cuff 8. The linking of all three cuffs 5, 7 and 8 to each other is accomplished through the use of bell crank 34, lever 35 and linkage means 36 in such a manner that distal forearm cuff 7 rotates when elbow 3 is flexed and extended. Connecting distal forearm cuff 7 and proximal forearm cuff 8 with a bell crank 34 that has its pivot axis 40 on cuff 8 enables varying of the degree a wrist 2 is turned by apparatus 1. This is accomplished by varying the distance D between the end 54 of link 36 and pivot axis 40. Moving end 54 closer to axis 40 increases the amount of outward wrist rotation, and moving end 54 and axis 40 apart decreases the outward wrist rotation. The degree of elbow flexion at which rotation of wrist 3 begins and ends can be adjusted by changing the location on humeral cuff 5 at which end 48 of leverage means 33 is connected.

It has thus been shown that by the practice of this invention apparatus and methods of turning a non-functioning wrist 2 when an elbow 3 is flexed or straightened can be customized to an individual's needs and adjusted as the needs change. Cumbersome springs and other mechanisms are not required, and apparatus 1 is sufficiently compact that a shirt can be worn over it. The use of leverage means 33 results in smooth steady rotation of wrist 2 commensurate with the flexing of elbow 3 rather than jerky or uneven rotation resulting from spring meachanisms that may snap into action. External actuators such as 62 are easily attached permitting use of apparatus 1 by persons not having a functioning elbow 3.

While the invention has been described with reference to particular embodiments, it is not intended to illustrate or describe herein all of the equivalent forms or ramifications thereof. Also, the words used are words of description rather than limitation, and various changes may be made without departing from the spirit or scope of the invention disclosed herein. It is intended that the appended claims cover all such changes as fall within the true spirit and scope of the invention.

What is claimed is:

1. Apparatus for rotating a human wrist about the longitudinal axis of the arm, comprising:
   A. a humeral cuff for receiving a human arm above its elbow, a proximal forearm cuff for receiving the arm below the elbow, and a distal forearm cuff for receiving the wrist;
   B. hinge means connecting said humeral cuff to said proximal forearm cuff for permitting medial and lateral pivoting of said humeral and proximal forearm cuffs when the elbow is flexed or extended;
   C. means connecting said distal forearm cuff to said proximal forearm cuff for permitting rotation of said distal forearm cuff relative to said proximal forearm cuff; and
   D. means, connected to said humeral cuff and to said proximal forearm cuff and to said distal forearm cuff for causing said distal forearm cuff to rotate the wrist when the elbow is flexed or extended.

2. The invention defined in claim 1, wherein said means for causing said distal forearm cuff to rotate comprises a bell crank having one end connected to said distal forearm cuff, another end connected to said humeral cuff, and a pivot axis on said proximal forearm cuff.

3. The invention defined in claim 2, further comprising linkage means connecting said bell crank to said humeral cuff, said linkage means having one end connected to said bell crank at a predetermined distance from said pivot axis.

4. The invention defined in claim 3, wherein said linkage means has an opposite end pivotally connected to said humeral cuff.

5. The invention defined in claim 4, wherein said distance between said one end of said linkage means and said pivot axis can be varied to change the amount the wrist is rotated by said distal forearm cuff.

6. The invention defined in claim 1, wherein said means for causing said distal forearm cuff to rotate comprises linkage means having one end pivotally connected to said humeral cuff.

7. The invention defined in claim 6, wherein said one end is connected to said humeral cuff by lever means having a turning point at a hinge joint connecting said humeral cuff to said proximal forearm cuff, said one end being attached adjacent an end of said lever means extending beyond said humeral cuff, and an opposite end of said lever means being attached to said humeral cuff.

8. The invention defined in claim 7, wherein a common line is defined on said lever means, said linkage means passes from one side of said common line to the other as the elbow is flexed and extended, said rotation of the wrist begins as said linkage means cross said common line in one direction and said rotation stops when said linkage means cross said common line in the opposite direction, said opposite end of said lever means can be attached to said humeral cuff at predetermined locations on an arc having said turning point at its center so as to change the angle of said common line with respect to said linkage means and thereby change the degree of elbow flexion at which turning of the wrist begins and ends.

9. The invention defined in claim 1, further comprising electronic range of motion apparatus having an actuator movable over a range of positions, said actuator having one end connected to said humeral cuff and an opposite end connected to said proximal forearm cuff for causing flexing or extention of the elbow joint.

10. Apparatus for rotating a human wrist about the longitudinal axis of the arm, comprising:
    A. rotatable means for attachment to the wrist;
    B. means for attachment to an arm above the wrist adjacent an elbow; and
    C. means for causing rotation of the wrist when the elbow is flexed or extended comprising:
       1. a bell crank having one end attached to said rotatable means and a pivot axis on said means for attachment to an arm, said pivot axis being located between the elbow and the wrist, and
       2. linkage means having one end attached to said bell crank between the elbow and the wrist at a predetermined distance from said pivot axis, the opposite end of said linkage means being connected to said means for attachment to an arm adjacent an elbow.

11. The invention defined in claim 10, further comprising said one end of said linkage means being attached to an end of lever means in such a manner that said one end of said linkage means is unmoved when said elbow is flexed or extended, said lever means defines a common line, said linkage means passing from one side of said common line to the other as the elbow joint is flexed or extended, said rotation of the wrist beginning as said linkage means crosses said common line in one direction and said rotation stopping when said linkage means crosses said common line in the opposite direction, said lever means having an opposite end attached to said means for attachement to an arm and a turning point between its ends, there being an arc on said means for attachment to said arm having said turning point at its center, and said opposite end of said lever means being attachable at different locations on said arc so as to change the angle of said common line with respect to said linkage means and thereby to change the degree of elbow flexion at which turning of the wrist begins and ends.

12. The invention defined in claim 10, wherein said distance between said one end of said linkage means and said pivot axis can be varied to change the amount the wrist is rotated by said rotatable means.

13. The invention defined in claim 10, further comprising electronic range of motion apparatus having an actuator movable over a range of positions, said actuator causing extension or flexing of the elbow.

14. The method of rotating a wrist about the longitudinal axis of a human arm, comprising the steps of:
    A. attaching a distal forearm cuff to the wrist;
    B. attaching a humeral cuff to the arm above its elbow;
    C. attaching a proximal forearm cuff to the arm below the elbow between said distal forearm cuff and said humeral cuff;
    D. hinging said humeral cuff to said proximal forearm cuff so that said humeral and proximal forearm cuffs pivot when the elbow is flexed or extended;
    E. connecting said distal forearm cuff to said proximal forearm cuff so that said distal forearm cuff can rotate relative to said proximal forearm cuff; and
    F. linking said humeral cuff to said proximal forearm cuff and said proximal forearm cuff to said distal forearm cuff in such a manner that said distal forearm cuff rotates the wrist when the elbow is flexed or extended.

15. The invention defined in claim 14, further comprising linking said distal forearm cuff to said proximal forearm cuff with a bell crank having a pivot axis on said proximal forearm cuff.

16. The invention defined in claim 15, further comprising linking said humeral cuff to said proximal forearm cuff with a linking having one end attached to said bell crank at a predetermined distance from said pivot axis and an opposite end pivotally connected to said humeral cuff.

17. The invention defined in claim 16, further comprising varying the amount of rotation of the wrist when the elbow is flexed or extended by changing said predetermined distance between said one end of said linkage and said pivot axis of said bell crank.

18. The invention defined in claim 17, further comprising increasing the amount the wrist rotates by moving said one end closer to said pivot axis, and decreasing the amount the wrist rotates by moving said one end further from said pivot axis.

19. The invention defined in claim 16, further comprising adjusting the degree of elbow flexion at which rotation of the wrist begins and ends by changing the location at which said opposite end of said linkage is connected to said humeral cuff.

20. The invention defined in claim 14, further comprising connecting one end of an electronic range of motion actuator to said humeral cuff, connecting the opposite end of said actuator to said proximal forearm cuff, and moving said actuator over a range of positions for causing flexing or extension of the elbow.

* * * * *